US012616725B2

(12) United States Patent
    Kim et al.

(10) Patent No.:    US 12,616,725 B2
(45) Date of Patent:        May 5, 2026

(54) BIFIDOBACTERIUM BREVE IDCC 4401 STRAIN AND ITS DEAD CELL ID-BBR4401 HAVING EXCELLENT ACID TOLERANCE AND BILE TOLERANCE AND PROPHYLACTIC OR THERAPEUTIC EFFECT ON DYSLIPIDEMIA

(71) Applicant: ILDONG HEALTHCARE CO., LTD., Gyeonggi-do (KR)

(72) Inventors: Min-Goo Kim, Seoul (KR); Don-Gil Lee, Seoul (KR); Tae-Yoon Kim, Seoul (KR)

(73) Assignee: ILDONG HEALTHCARE CO., LTD., Gyeonggi-do (KR)

( * ) Notice: Subject to any disclaimer, the term of this patent is extended or adjusted under 35 U.S.C. 154(b) by 419 days.

(21) Appl. No.: 18/148,955

(22) Filed: Dec. 30, 2022

(65) Prior Publication Data

US 2023/0285474 A1      Sep. 14, 2023

Related U.S. Application Data

(63) Continuation      of      application      No. PCT/KR2021/007117, filed on Jun. 8, 2021.

(30) Foreign Application Priority Data

Jun. 30, 2020      (KR) ........................ 10-2020-0080588

(51) Int. Cl.
    *A61K 35/745*      (2015.01)
    *A23K 10/18*      (2016.01)
    *A23L 33/135*      (2016.01)
    *A61K 35/00*      (2006.01)
    *A61P 3/06*      (2006.01)
    *C12N 1/20*      (2006.01)
    *C12N 1/205*      (2026.01)
    *C12N 1/36*      (2006.01)
    *C12R 1/01*      (2006.01)

(52) U.S. Cl.
    CPC ............ *A61K 35/745* (2013.01); *A23K 10/18* (2016.05); *A23L 33/135* (2016.08); *A61P 3/06* (2018.01); *C12N 1/205* (2021.05); *C12N 1/36* (2013.01); *A23V 2400/519* (2023.08); *A61K 2035/115* (2013.01); *C12R 2001/01* (2021.05)

(58) Field of Classification Search
    None
    See application file for complete search history.

(56) References Cited

U.S. PATENT DOCUMENTS

2004/0208859 A1      10/2004    Yokota et al.

FOREIGN PATENT DOCUMENTS

| JP | 2006-217879 | A | 8/2006 |
| KR | 10-2004-0030955 | A | 4/2004 |
| KR | 10-2004-0089987 | A | 10/2004 |
| WO | WO 2021/177798 | A1 | 9/2021 |

OTHER PUBLICATIONS

Bordoni et al. "Cholesterol-lowering probiotics: in vitro selection and in vivo testing of bifidobacterial," Applied Microbiology and Biotechnology, (2013) vol. 97, pp. 8273-8281.

Kim et al. "Bifidobacterium breve strain IDCC 4401 16S ribosomal RNA gene, partial sequence," GenBank Accession No. KP32541, deposited Apr. 2015, available online: https://www.ncbi.nlm.nih. gov/nuccore/KP325411.

Office Action corresponding to Australian Patent Application No. 2021299360 dated Jun. 13, 2024.

Seo et al. "Development of Probiotic Products and Challenges," KSBB Journal, (2010) vol. 25, pp. 303-310.

Shin et al. "Efficacy and safety of GQ-lab daily in patients with irritable bowel syndrome: a randomized, double-blind, placebo-controlled, parallel-group study," Neurogastroenterology & Motility, (2019) vol. 31, Abstract No. 135, p. 99.

Office Action corresponding to Japanese Patent Application No. 2022-579911 dated Mar. 12, 2025.

Bifidobacterium breve IDCC 4401 Cholesterol improvement effect, effective intake, and human application study to confirm safety, non-official translation (Internet Webpage, Seoul Medical University/Seoul National University Hospital Medical Research Ethics Review Committee. (2018) https://cris.hih.go.kr/cris/search/detailSearch.do/16716.

Ildong Bioscience, Quadruple-coated Probiotics—Bifidobacterium breve IDCC44 (2018) https://www.gobizkorea.com/user/goods /frontGoodsDetail.do?goods_no=GS2018091155262.

International Search Report corresponding to International Application No. PCT/KR2021/007117 dated Sep. 15, 2021.

(Continued)

*Primary Examiner* — S. Devi

(74) *Attorney, Agent, or Firm* — Jenkins, Taylor & Hunt, P.A.

(57)        ABSTRACT

The present invention relates to a novel *Bifidobacterium breve* IDCC 4401 strain (accession number: KCTC13169BP) and dead cell thereof ID-BBR4401, which are superb in acid tolerance and bile tolerance and have a preventive or therapeutic effect on dyslipidemia. Having not only an excellent effect of reducing a cholesterol level in the body but alto a very high level of acid tolerance and bile tolerance in contrast to previously known *B. breve*, the novel *Bifidobacterium breve* IDCC 4401 strain (accession number: KCTC13169BP) of the present invention well exhibits the functionality that the strain has in the digestive duct of animals (especially humans), has an excellent growth potential, and provides sustainable and effective functionality of reducing a level of cholesterol in vivo.

1 Claim, 7 Drawing Sheets

Specification includes a Sequence Listing.

(56)         References Cited

OTHER PUBLICATIONS

Joo., et al. "Bifidobacterium breve strain IDCC 4401 improves dyslipidemia in rat model", International Journal of Clinical and Experimental Medicine, (2020) vol. 13, No. 6, pp. 4137-4144.
CRIS Registration No. KCT0003040, Study for evaluation of cholesterol lowering effect, dose and safety of Bifidobacterium breve IDCC 4401, CRIS search [online], uploaded on May 15, 2020, CRIS, <URL: https://cris.nih.go.kr/cris/search/listDetail.do>, retrieval date Mar. 6, 2025.
Office Action corresponding to U.S. Appl. No. 18/148,901 dated May 1, 2025.

Live cell

Dead cell

Live cell

Dead cell

BIFIDOBACTERIUM BREVE IDCC 4401 STRAIN AND ITS DEAD CELL ID-BBR4401 HAVING EXCELLENT ACID TOLERANCE AND BILE TOLERANCE AND PROPHYLACTIC OR THERAPEUTIC EFFECT ON DYSLIPIDEMIA

CROSS-REFERENCE TO RELATED APPLICATIONS

This application is a continuation of and claims priority to PCT International Patent Application Serial No. PCT/KR2021/007117, filed Jun. 8, 2021, which itself claims priority to Korean Patent Application No. 10-2020-0080588, filed Jun. 30, 2020, the disclosures of both of which are incorporated by reference herein in their entireties.

REFERENCE TO SEQUENCE LISTING XML

The Sequence Listing XML associated with the instant disclosure has been electronically submitted to the United States Patent and Trademark Office via the Patent Center as a 3,730 byte UTF-8-encoded XML file created on Dec. 30, 2022 and entitled "3204_24_PCT_US". The Sequence Listing submitted via Patent Center is hereby incorporated by reference in its entirety.

TECHNICAL FIELD

The present invention relates to a novel *Bifidobacterium breve* IDCC 4401 strain (accession number: KCTC13169BP) and dead cell thereof ID-BBR4401 having excellent acid tolerance and bile tolerance and a preventive or therapeutic effect on dyslipidemia, and more particularly, to uses for prevention, improvement and treatment of dyslipidemia of the novel *Bifidobacterium breve* IDCC 4401 strain or dead cell thereof ID-BBR4401 and a composition for controlling intestinal functions, a probiotic composition, a feed composition and a fermented product comprising the strain as an active ingredient.

BACKGROUND

Dyslipidemia refers to a state in which total cholesterol, low-density lipoprotein (LDL) cholesterol, and triglycerides are increased, or high-density lipoprotein (HDL) cholesterol is decreased in the blood. The dyslipidemia is a broad disease name that includes all hyperlipidemia, hypercholesterolemia, and hypertriglyceridemia, and among them, hypercholesterolemia refers to a disease in which total cholesterol and low-density lipoprotein cholesterol are high in a state in which cholesterol is increased in the blood. The hypercholesterolemia is defined when the serum cholesterol level is highest due to cholesterol metabolism disorder or excessive intake of cholesterol.

Cholesterol is an essential component of the human body, but its metabolic abnormality is greatly related to the onset of adult diseases, especially arteriosclerosis. It is known that about 140 g of cholesterol is present in adults, about 1% of which is metabolized daily, and an important metabolite is bile acids. The bile acids are not only a metabolite of cholesterol, but also form micelles with cholesterol-containing lipids in the digestive tract to promote its absorption. Since the bile acids are essential for the formation of micelles, the absence of bile acids interferes with the absorption of fat-soluble substances such as lipids and vitamins. Secreted bile acids represent the enterohepatic circulation where the bile acids are absorbed from the intestinal tract, returned to the liver, and secreted back into the bile. It is known that when the bile acids are not reabsorbed but released during such circulation, the requirement of cholesterol, which is a precursor, to biosynthesize new bile acids also increases to lower cholesterol levels in vivo.

In general, hypercholesterolemia is determined when the cholesterol concentration in serum (plasma) is 220 to 250 mg/dL or higher, or when the low-density lipoprotein cholesterol concentration is 160 mg/dL or higher. If the high cholesterol state continues for a long time, the cholesterol is deposited on the arterial wall to cause atherosclerosis and cause myocardial infarction or cerebral thrombosis. In addition, the cholesterol is deposited in connective tissue to cause xanthomas or easily cause cholelithiasis, including cholesterin stones.

Some patients with hypercholesterolemia may use drug treatment depending on the severity of the symptoms, but statin-based drugs are the most commonly used. The statin-type drugs are HMG-CoA reductase inhibitors and have the effect of inhibiting cholesterol synthesis (Ki-Hun Han et al., Grounds for statin clinical studies, the Korean Society of Lipid and Arteriosclerosis Treatment Guidelines Committee (2010) pp. 14~15). Statins decrease low-density lipoprotein cholesterol and triglycerides in a dose-dependent manner and partially increase high-density lipoprotein cholesterol. Side effects of these statins include indigestion, headache, fatigue, joint pain, and the like, and if there are muscle symptoms due to the risk of myopathy, a blood test is required, and because of a possibility of liver dysfunction, a liver function test is required before prescription, after 2 to 3 months of administration, and then at 1-year intervals.

Accordingly, research on safer materials without side effects is being conducted, and recently, many studies on functional foods that can be combined with diet have been conducted. Accordingly, part of the effort to improve hypercholesterolemia has been attempted in the field of research using probiotics strains.

Meanwhile, a dead cell of lactic acid bacteria is an opposite concept of a live cell, and is a form in which the growth of bacteria is prevented from occurring by heat treatment of live cells and metabolites obtained through fermentation (Jae-Gu Seo, et al., Development of Probiotic Products and Challenges, KSBB Journal 2010. 25: 303~310). In the case of actual live cells, many of the live cells die when reaching the intestine after oral administration. This is particularly noticeable when the lactic acid bacteria are not resistant to the internal environment of the digestive tract, such as acid tolerance and bile tolerance. When the live cells are killed in a general manner due to the environment of the digestive system in vivo and the like, some or all of various activities of the live cells may be changed. Accordingly, when the live cells are administered in anticipation of the benefit of a specific desired physiological activity, the activity may not be stably achieved in the body as expected depending on the type of the specific desired physiological activity and bacteria. This may lead to an excessive dosage, which may result in problems such as side effects. In addition, since the live cells may deteriorate depending on a temperature during storage, there may be a problem in maintaining the stability of the activity of probiotic agents in terms of preservation.

Technologies using dead cells have been reported to overcome the problems of these probiotic agents, but high specificity is required depending on various factors, such as a type of specific cells and a method of killing cells, according to a type of physiological activity to be obtained in a technique of actually using dead cells.

SUMMARY

Therefore, the present inventors found a novel *Bifidobacterium breve* IDCC 4401 strain (accession number: KCTC13169BP) having excellent cholesterol binding ability while studying lactic acid bacteria-made agents that exhibited reduction ability of cholesterol at stable and high levels when introduced into the body, confirmed that the strain not only had very excellent acid tolerance and bile tolerance, but also a dead cell (that is, ID-BBR4401) of the *Bifidobacterium breve* IDCC 4401 strain prepared therefrom exhibited an effect of reducing cholesterol at a higher level than live cells in a dyslipidemia animal model, and then completed the present invention.

An object of the present invention is to provide a *Bifidobacterium breve* IDCC 4401 strain (accession number: KCTC13169BP) or dead cell thereof having acid tolerance and bile tolerance and a preventive or therapeutic effect on dyslipidemia.

Another object of the present invention is to provide a pharmaceutical composition for preventing or treating dyslipidemia comprising at least one of a *Bifidobacterium breve* IDCC 4401 strain (accession number: KCTC13169BP), culture thereof or a *Bifidobacterium breve* IDCC 4401 dead cell as an active ingredient.

In addition, another object of the present invention is to provide a pharmaceutical composition for preventing or treating dyslipidemia consisting of at least one of a *Bifidobacterium breve* IDCC 4401 strain (accession number: KCTC13169BP), culture thereof or a *Bifidobacterium breve* IDCC 4401 dead cell.

In addition, another object of the present invention is to provide a pharmaceutical composition for preventing or treating dyslipidemia essentially consisting of at least one of a *Bifidobacterium breve* IDCC 4401 strain (accession number: KCTC13169BP), culture thereof or a *Bifidobacterium breve* IDCC 4401 dead cell.

Yet another object of the present invention is to provide a food composition for preventing or improving dyslipidemia comprising at least one of a *Bifidobacterium breve* IDCC 4401 strain (accession number: KCTC13169BP), culture thereof or a *Bifidobacterium breve* IDCC 4401 dead cell as an active ingredient.

In addition, yet another object of the present invention is to provide a food composition for preventing or improving dyslipidemia consisting of at least one of a *Bifidobacterium breve* IDCC 4401 strain (accession number: KCTC13169BP), culture thereof or a *Bifidobacterium breve* IDCC 4401 dead cell.

In addition, yet another object of the present invention is to provide a food composition for preventing or improving dyslipidemia essentially consisting of at least one of a *Bifidobacterium breve* IDCC 4401 strain (accession number: KCTC13169BP), culture thereof or a *Bifidobacterium breve* IDCC 4401 dead cell.

Yet another object of the present invention is to provide a health functional food composition for preventing or improving dyslipidemia comprising at least one of a *Bifidobacterium breve* IDCC 4401 strain (accession number: KCTC13169BP), culture thereof or a *Bifidobacterium breve* IDCC 4401 dead cell as an active ingredient.

In addition, yet another object of the present invention is to provide a health functional food composition for preventing or improving dyslipidemia consisting of at least one of a *Bifidobacterium breve* IDCC 4401 strain (accession number: KCTC13169BP), culture thereof or a *Bifidobacterium breve* IDCC 4401 dead cell.

In addition, yet another object of the present invention is to provide a health functional food composition for preventing or improving dyslipidemia essentially consisting of at least one of a *Bifidobacterium breve* IDCC 4401 strain (accession number: KCTC13169BP), culture thereof or a *Bifidobacterium breve* IDCC 4401 dead cell.

Yet another object of the present invention is to provide a composition for controlling intestinal functions, a probiotic composition, a feed composition, and a fermented product comprising a *Bifidobacterium breve* IDCC 4401 strain (accession number: KCTC13169BP) or culture thereof as an active ingredient.

In addition, yet another object of the present invention is to provide a composition for controlling intestinal functions, a probiotic composition, a feed composition, and a fermented product consisting of a *Bifidobacterium breve* IDCC 4401 strain (accession number: KCTC13169BP) or culture thereof.

In addition, yet another object of the present invention is to provide a composition for controlling intestinal functions, a probiotic composition, a feed composition, and a fermented product essentially consisting of a *Bifidobacterium breve* IDCC 4401 strain (accession number: KCTC13169BP) or culture thereof.

Yet another object of the present invention is to provide a use of a *Bifidobacterium breve* IDCC 4401 strain (accession number: KCTC13169BP), culture thereof or a *Bifidobacterium breve* IDCC 4401 dead cell for preparing an agent for treating dyslipidemia.

Yet another object of the present invention is to provide a method for treating dyslipidemia comprising administering an effective amount of an agent comprising at least one of a *Bifidobacterium breve* IDCC 4401 strain (accession number: KCTC13169BP), culture thereof or a *Bifidobacterium breve* IDCC 4401 dead cell to a subject in need thereof.

In order to achieve the object of the present invention, there is provided a *Bifidobacterium breve* IDCC 4401 strain (accession number: KCTC13169BP) or dead cell thereof having acid tolerance and bile tolerance and a preventive or therapeutic effect on dyslipidemia.

In order to achieve another object of the present invention, there is provided a pharmaceutical composition for preventing or treating dyslipidemia comprising at least one of a *Bifidobacterium breve* IDCC 4401 strain (accession number: KCTC13169BP), culture thereof or a *Bifidobacterium breve* IDCC 4401 dead cell as an active ingredient.

In addition, the present invention provides a pharmaceutical composition for preventing or treating dyslipidemia consisting of at least one of a *Bifidobacterium breve* IDCC 4401 strain (accession number: KCTC13169BP), culture thereof or a *Bifidobacterium breve* IDCC 4401 dead cell.

In addition, the present invention provides a pharmaceutical composition for preventing or treating dyslipidemia essentially consisting of at least one of a *Bifidobacterium breve* IDCC 4401 strain (accession number: KCTC13169BP), culture thereof or a *Bifidobacterium breve* IDCC 4401 dead cell.

In order to achieve yet another object of the present invention, there is provided a food composition for preventing or improving dyslipidemia comprising at least one of a *Bifidobacterium breve* IDCC 4401 strain (accession number: KCTC13169BP), culture thereof or a *Bifidobacterium breve* IDCC 4401 dead cell as an active ingredient.

In addition, the present invention provides a food composition for preventing or improving dyslipidemia consisting of at least one of a *Bifidobacterium breve* IDCC 4401 strain (accession number: KCTC13169BP), culture thereof or a *Bifidobacterium breve* IDCC 4401 dead cell.

In addition, the present invention provides a food composition for preventing or improving dyslipidemia essentially consisting of at least one of a *Bifidobacterium breve* IDCC 4401 strain (accession number: KCTC13169BP), culture thereof or a *Bifidobacterium breve* IDCC 4401 dead cell.

In order to achieve yet another object of the present invention, there is provided a health functional food composition for preventing or improving dyslipidemia comprising at least one of a *Bifidobacterium breve* IDCC 4401 strain (accession number: KCTC13169BP), culture thereof or a *Bifidobacterium breve* IDCC 4401 dead cell as an active ingredient.

In addition, the present invention provides a health functional food composition for preventing or improving dyslipidemia consisting of at least one of a *Bifidobacterium breve* IDCC 4401 strain (accession number: KCTC13169BP), culture thereof or a *Bifidobacterium breve* IDCC 4401 dead cell.

In addition, the present invention provides a health functional food composition for preventing or improving dyslipidemia essentially consisting of at least one of a *Bifidobacterium breve* IDCC 4401 strain (accession number: KCTC13169BP), culture thereof or a *Bifidobacterium breve* IDCC 4401 dead cell.

In order to achieve yet another object of the present invention, there are provided a composition for controlling intestinal functions, a probiotic composition, a feed composition, and a fermented product comprising a *Bifidobacterium breve* IDCC 4401 strain (accession number: KCTC13169BP) or culture thereof as an active ingredient.

In addition, the present invention provides a composition for controlling intestinal functions, a probiotic composition, a feed composition, and a fermented product consisting of a *Bifidobacterium breve* IDCC 4401 strain (accession number: KCTC13169BP) or culture thereof.

In addition, the present invention provides a composition for controlling intestinal functions, a probiotic composition, a feed composition, and a fermented product essentially consisting of a *Bifidobacterium breve* IDCC 4401 strain (accession number: KCTC13169BP) or culture thereof.

In order to achieve yet another object of the present invention, there is provided a use of a *Bifidobacterium breve* IDCC 4401 strain (accession number: KCTC13169BP), culture thereof or a *Bifidobacterium breve* IDCC 4401 dead cell for preparing an agent for treating dyslipidemia.

In order to achieve yet another object of the present invention, there is provided a method for treating dyslipidemia comprising administering an effective amount of an agent comprising at least one of a *Bifidobacterium breve* IDCC 4401 strain (accession number: KCTC13169BP), culture thereof or a *Bifidobacterium breve* IDCC 4401 dead cell to a subject in need thereof.

6

Figure 2:

FIG. 2 is a raw material photograph of ID-BBR4401, which is a dead cell preparation of *Bifidobacterium breve* IDCC 4401 having an effect of improving hypercholesterolemia.

Figure 3:
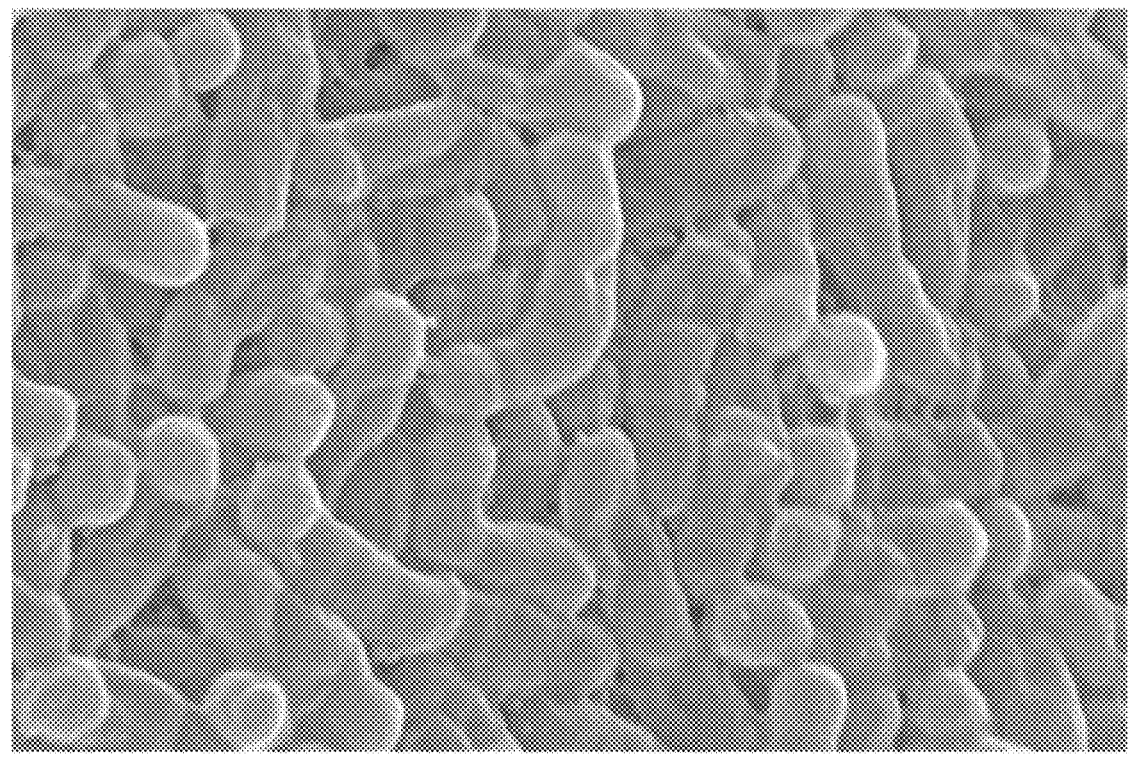

FIG. 3 is a scanning electron micrograph of ID-BBR4401 having an effect of improving hypercholesterolemia.

Figure 4:
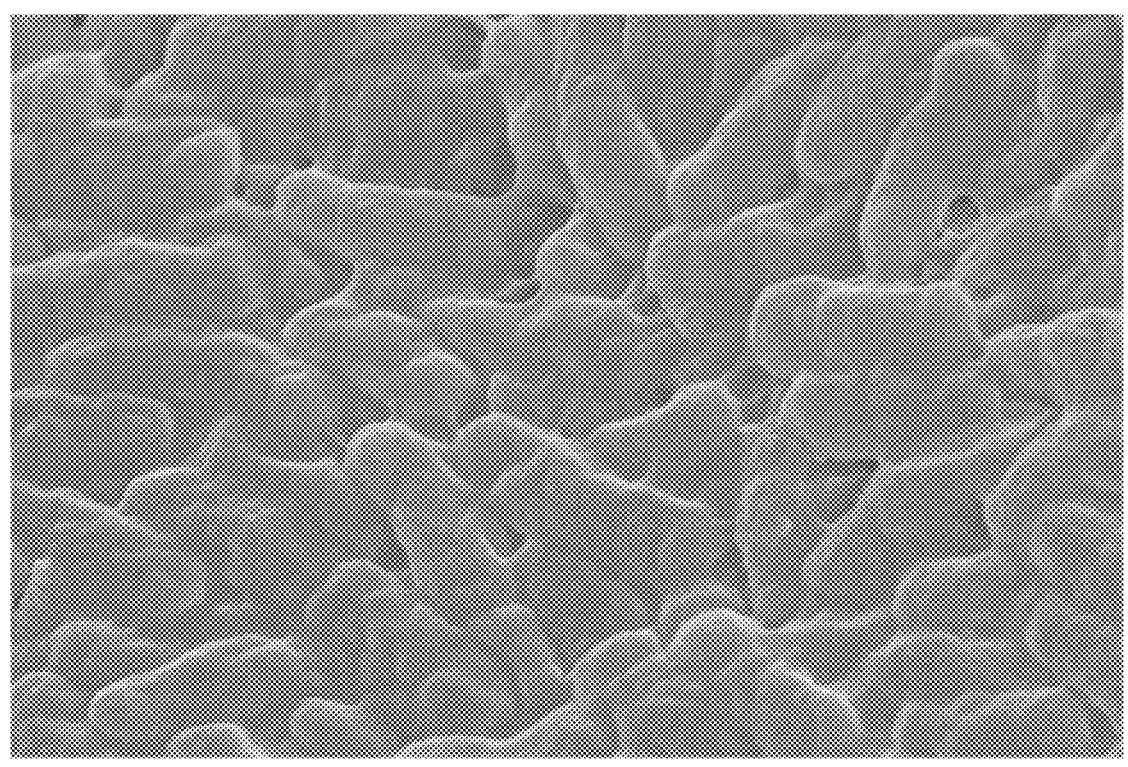

FIG. 4 is a scanning electron micrograph of ID-BBR4401 binding to cholesterol.

Figure 5:
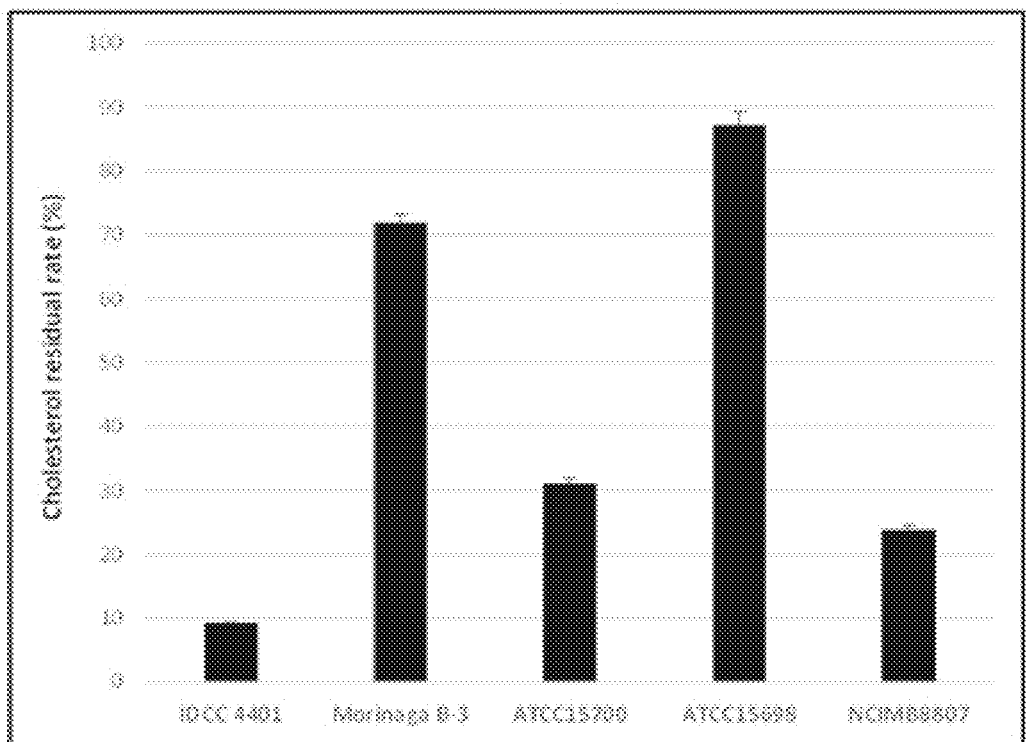
Figure 5:
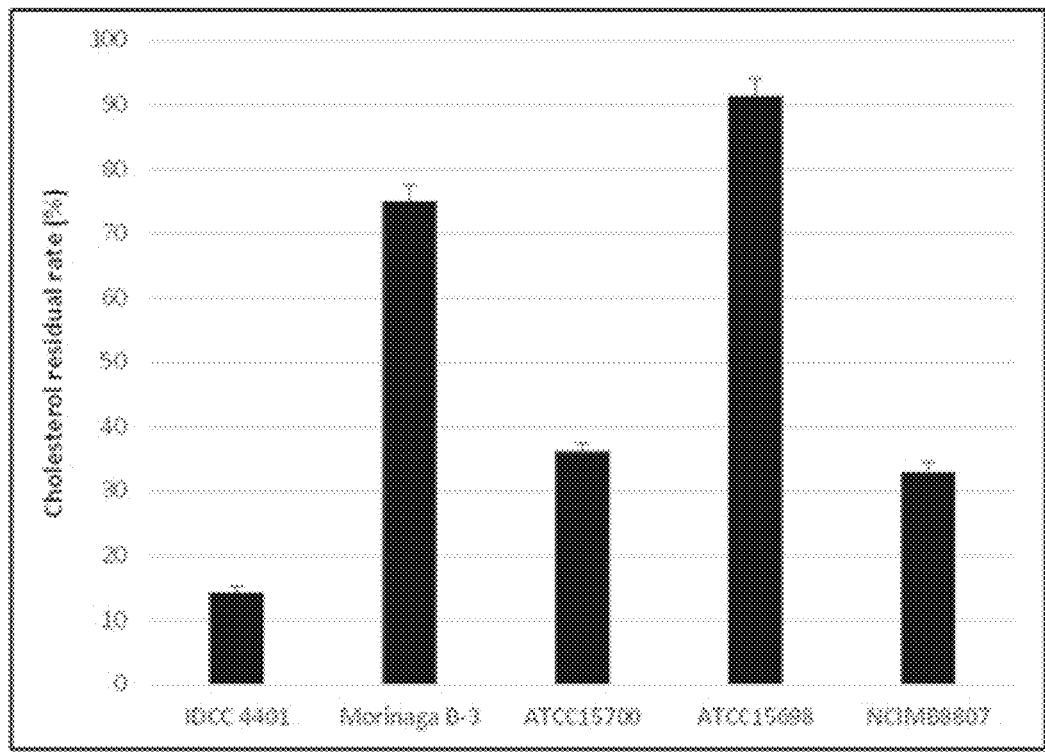

FIG. 5 is a series of bar graphs comparing and evaluating the cholesterol-reducing ability of various bacterial species, including the novel strain of the present invention. The top panel shows the results of using live cell preparations and the bottom panel shows the results of using dead cell preparations.

Figure 6:
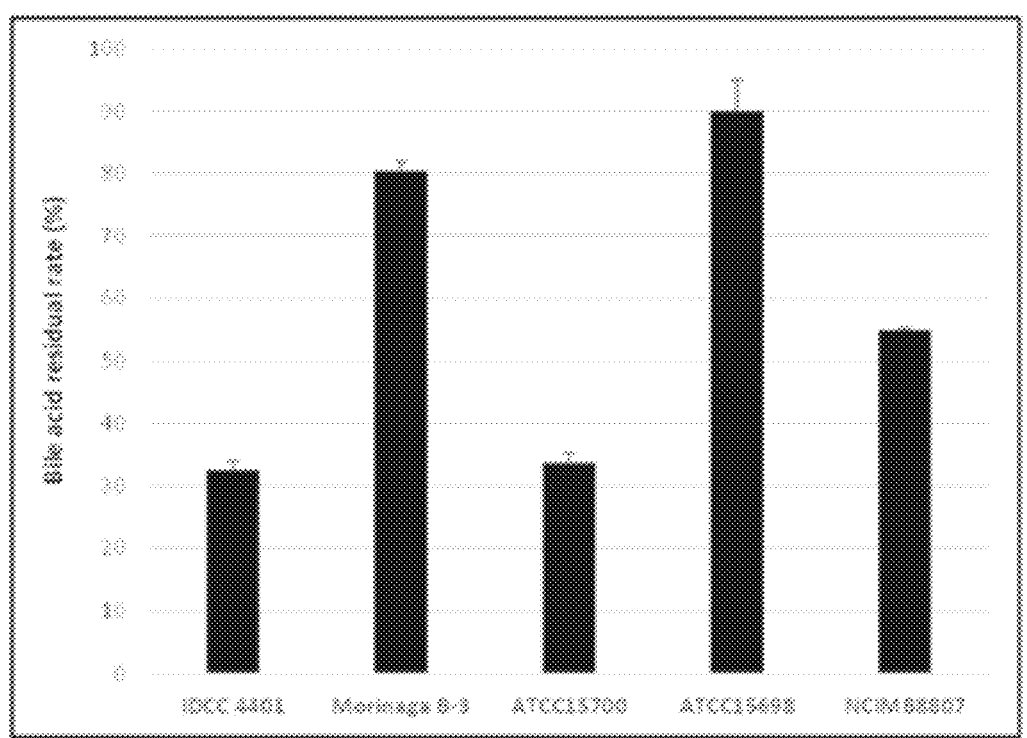
Figure 6:
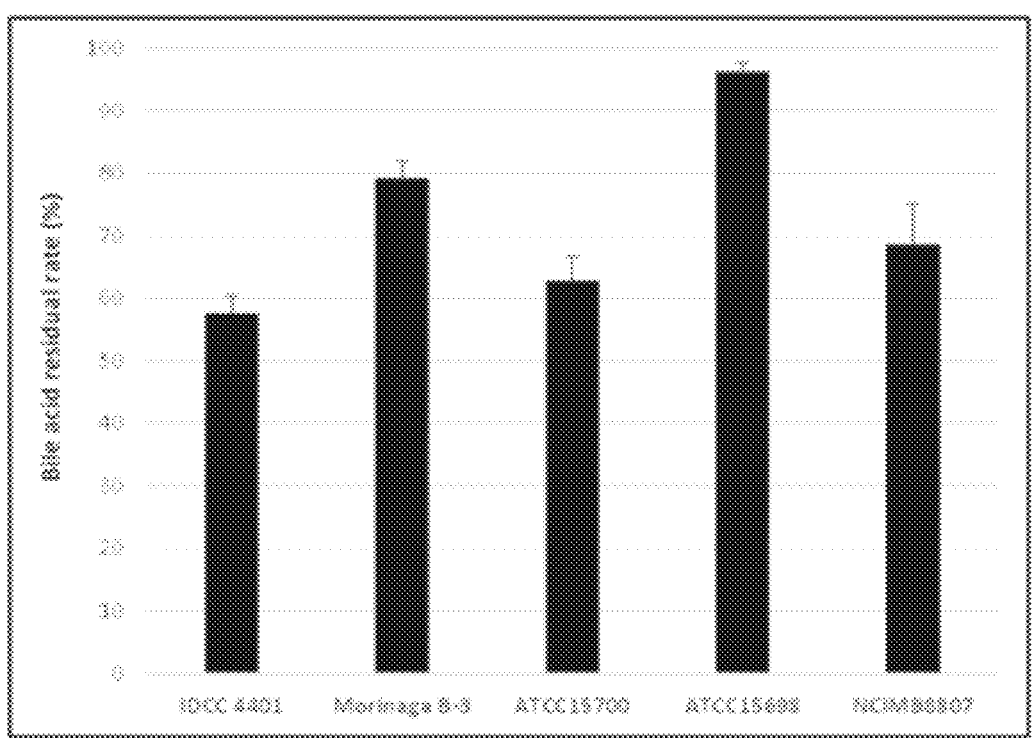

FIG. 6 is a series of bar graphs comparing and evaluating the bile acid-reducing ability of various bacterial species, including the novel strain of the present invention. The top panel shows the results of using live cell preparations and the bottom panel shows the results of using dead cell preparations.

Figure 7:
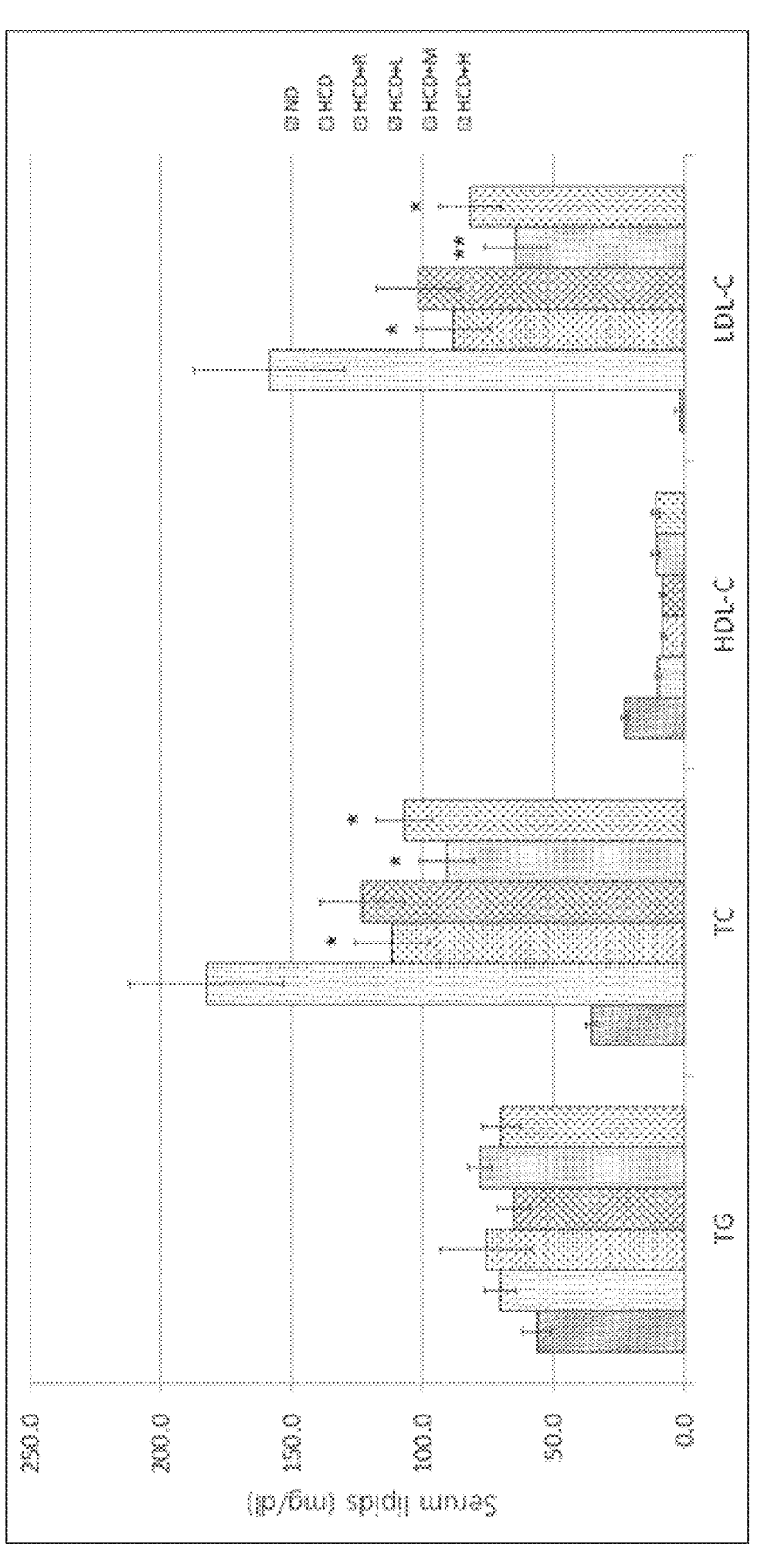

FIG. 7 is a is a series of bar graphs showing effects of ID-BBR4401, which is a dead cell preparation of *Bifidobacterium breve* IDCC 4401, on blood lipids in a dyslipidemia (hyperlipidemia) animal model. TG: triglyceride; TC: in vivo total cholesterol; HDL-C: high density lipoprotein cholesterol; LDL-C: low density lipoprotein cholesterol.

Figure 8:
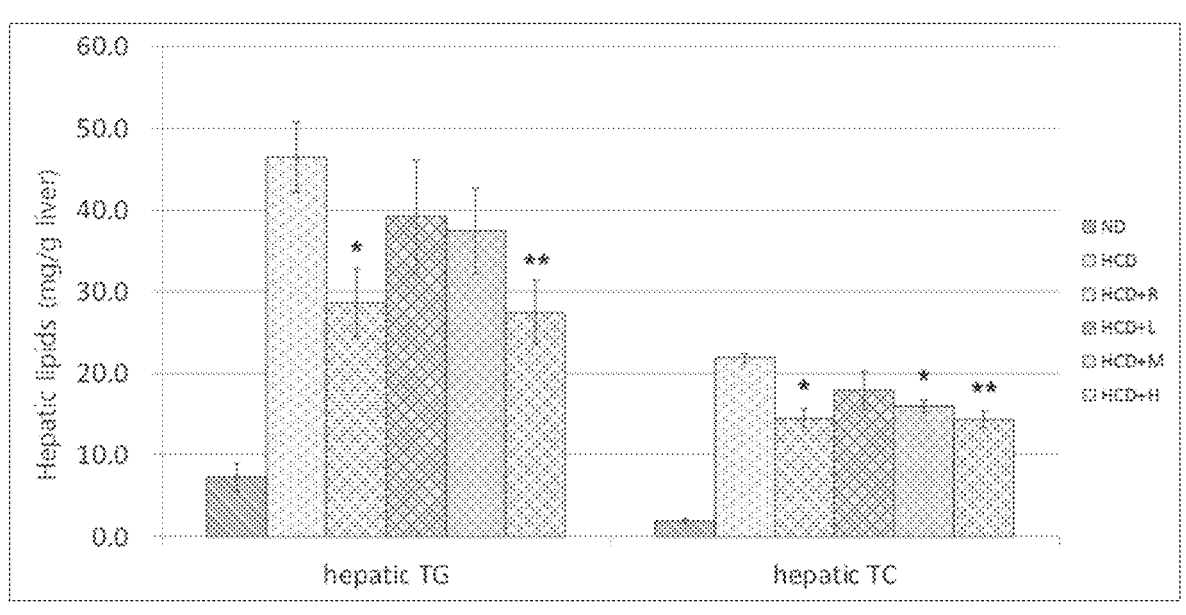

FIG. 8 is a series of bar graphs showing effects of ID-BBR4401, which is a dead cell preparation of *Bifidobacterium breve* IDCC 4401, on hepatic lipids in a dyslipidemia (hyperlipidemia) animal model. TG: triglyceride; TC: in vivo total cholesterol.

Figure 9:
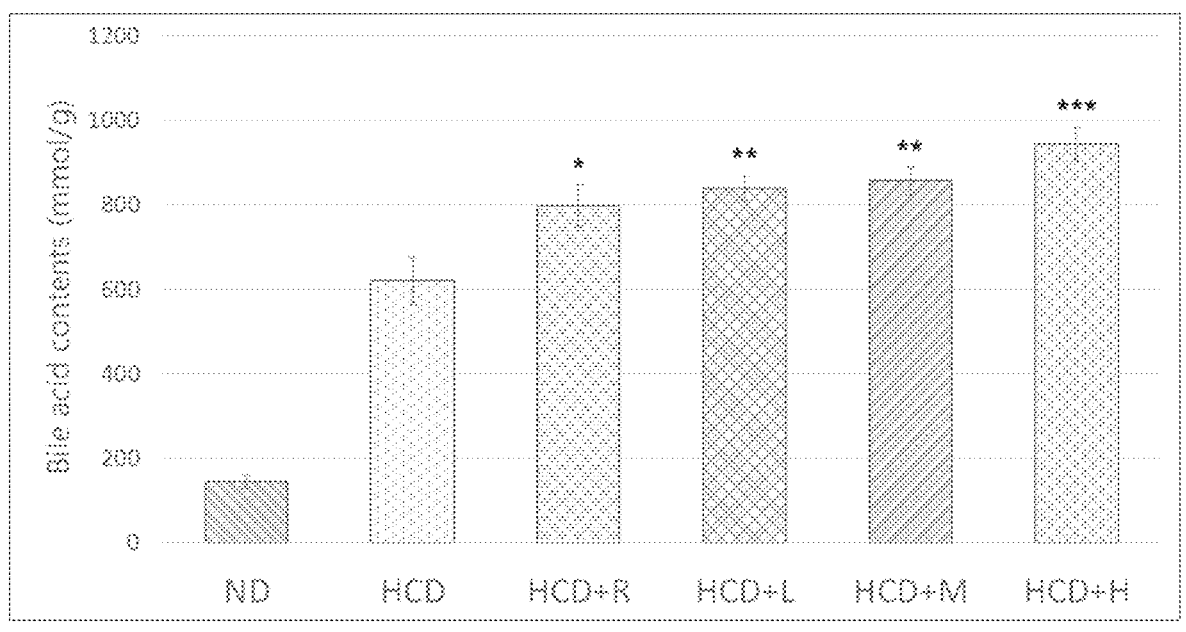

FIG. 9 is a series of bar graphs showing effects of ID-BBR4401, which is a dead cell preparation of *Bifidobacterium breve* IDCC 4401, on amounts of bile acids in feces in a dyslipidemia (hyperlipidemia) animal model. ND: normal; HCD: vehicle (only high-fat diet; HCD+R: positive control (Rosuvastatin 10 mg/kg/2 mL administration; HCD-L: ID-BBR4401 $1 \times 10^6$ cells/rat administered group; HCD+M: ID-BBR4401 $1 \times 10^7$ cells/rat administered group; HCD+H: ID-BBR4401 $1 \times 10^8$ cells/rat administered group.

DETAILED DESCRIPTION

Hereinafter, the present invention will be described in detail.

The present invention provides a *Bifidobacterium breve* IDCC 4401 strain (accession number: KCTC13169BP) or dead cell thereof having acid tolerance and bile tolerance and a preventive or therapeutic effect on dyslipidemia.

The term 'dyslipidemia' as used herein refers to a state in which total cholesterol, low-density lipoprotein (LDL) cholesterol, and triglycerides are increased, or high-density lipoprotein (HDL) cholesterol is decreased in the blood, and means including all hyperlipidemia, hypercholesterolemia, hypertriglyceridemia, and the like. Preferably, in the present invention, the dyslipidemia may be hypercholesterolemia.

The *Bifidobacterium breve* IDCC 4401 strain is characterized to not only have an excellent adsorption capacity for cholesterol itself, but also have its BSH activity and its binding ability of cholesterol to bile acids as a precursor. Accordingly, the *Bifidobacterium breve* IDCC 4401 strain is characterized to not only have an excellent function of reducing (lowering) cholesterol in the body, but also have excellent acid tolerance and bile tolerance. This is well shown in embodiments of the present invention.

In an embodiment of the present invention, it was confirmed that a novel strain *B. breve* IDCC 4401 of the present invention has significantly superior cholesterol binding ability compared to other strain species and the same strain species shown to have cholesterol binding ability in the related art.

In another embodiment of the present invention, it was confirmed that the novel strain *B. breve* IDCC 4401 of the present invention not only has excellent growth ability compared to other *B. breve* strains even in a highly acidic environment of pH 2.5, but also shows excellent growth ability in a high-concentration bile environment of 0.5%. Considering that it is generally known that the concentration of bile in the small intestine is 0.06%, the novel strain of the present invention has very excellent bile tolerance.

The '*Bifidobacterium breve* IDCC 4401 strain' includes not only live cells themselves obtained from a culture medium, but also any processed forms (particularly, processed forms of live cells) of lactic acid bacteria known to those skilled in the art, for example, a dried product, a frozen product, etc., but is not limited thereto.

In the present invention, the 'dead cell of the *Bifidobacterium breve* IDCC 4401 strain' may also be referred to as 'ID-BBR4401' in the present specification, and the dead cell of the present invention may be prepared by a method of killing including heat treatment (by heat treatment). The heat treatment may be performed on only live cells isolated and obtained from the culture solution, or may be performed on a culture solution containing the live cells. The heat treatment temperature is not particularly limited as long as the properties of the cells are maintained and other general bacteria are sterilized, but the temperature condition may be 80° C. to 150° C., preferably 80° C. to 110° C.

The heat treatment time is not particularly limited as long as those skilled in the art can obtain the desired manufacturing quality in consideration of the temperature condition, but may be preferably 1 hour to 2 hours. When heated for less than 1 hour, the bacteria may not be completely killed, and when heated for a long time of more than 2 hours, the surface of the bacteria may be denatured and the desired effect may not be exhibited.

During the heat treatment process for preparing the dead cell, those skilled in the art may add any pretreatment or additional conditions for preparation efficiency without affecting the cholesterol-reducing ability of the dead cell of the present invention. For example, distilled water may be added to and mixed with the live cells before the heat treatment. When the amount of distilled water is added less than the weight of the cells or not added, the color of the raw material becomes darker due to the influence of heat during heating, but when the amount of distilled water is added 1 to 2 times or more of the weight of the cells, the color of the raw material does not change and becomes sensually superior.

Most preferably, the dead cell of the present invention may be prepared by heating live cells in water at 80° C. to 90° C. More specifically, the dead cells may be prepared by centrifuging the culture solution of the *Bifidobacterium breve* IDCC 4401 strain to be separated into live cells and a culture filtrate, adding and suspending distilled water 1 to 2 times greater than the weight of the separated *Bifidobacterium breve* IDCC 4401 live cells, and then heating the live cells at 80° C. to 90° C.

The dead cells may be subjected to any additional process for the production of dead cell agents (formulations), and for example, concentration, drying, etc. may be performed. The type of drying is not particularly limited as long as the drying is a method used for drying lactic acid bacteria in the art, but may be, for example, heat (air) drying or freeze drying.

The dead cell ID-BBR4401 of the *Bifidobacterium breve* IDCC 4401 strain of the present invention is characterized by exhibiting a cholesterol reduction effect at a stable and high level. In particular, even though the *Bifidobacterium breve* IDCC 4401 strain of the present invention, unlike other *B. breve* strains, is killed by heat treatment, (considering that the number of live cells increases during the cultivation period) it is characterized that the ability to bind cholesterol is excellent at the same level as live cells. In addition, the dead cell ID-BBR4401 has a high level of binding ability with bile acids, and shows a remarkable effect in release of bile acids in vitro. The fact that ID-BBR4401 binds to conjugated bile acid to be released to the body is distinguished from a mechanism in which lactic acid bacteria probiotics known to have cholesterol-lowering ability in the related art deconjugate bile acids secreted into the small intestine through bile salt hydrolase (BSH) activity to be converted to free bile acids and these free bile acids are less reabsorbable than conjugated bile acids to be released out of the body.

As a result, the dead cell ID-BBR4401 of the present invention not only has a very excellent reducing effect of cholesterol in vivo, particularly LDL-cholesterol, but also has a remarkable reducing effect of triglycerides in vivo (especially, in the liver), thereby exhibiting an excellent effect of preventing and treating dyslipidemia.

This is well shown in embodiments of the present invention.

In an embodiment of the present invention, live cells of *B. breve* strains known to have a cholesterol-lowering effect in the related art and the IDCC 4401 strain of the present invention are killed by heat treatment in the same manner, and then cholesterol-lowering ability (cholesterol adhesion ability) thereof was measured. As a result, considering that live cells grow during the culture period and the number of live cells is relatively larger than that of dead cells, it was confirmed that the *Bifidobacterium breve* IDCC 4401 dead cell ID-BBR4401 of the present invention has the lowest residual cholesterol per same cell unit number, which has significantly better cholesterol-lowering ability (cholesterol adhesion ability) compared to other *B. breve* dead cells, and particularly, ID-BBR4401 of the present invention is very remarkably superior in cholesterol-lowering ability even compared to live cells of other *B. breve* strains.

In another embodiment of the present invention, the effect of the dead cell ID-BBR4401 on a dyslipidemia (hyperlipidemia) animal model was confirmed. As a result, it was confirmed that ID-BBR4401 of the present invention exhibits an effect of not only reducing in vivo cholesterol (TC), particularly LDL-cholesterol, but also reducing a triglyceride (TG) level in the liver.

Accordingly, the present invention provides a composition or a health functional food composition for preventing, improving, or treating dyslipidemia comprising at least one of a *Bifidobacterium breve* IDCC 4401 strain (accession number: KCTC13169BP), culture thereof or a *Bifidobacterium breve* IDCC 4401 dead cell as an active ingredient.

In the present invention, the term 'culturing' refers to all actions performed to grow microorganisms under appropriately artificially controlled environmental conditions. In the present invention, as a concept including 'fermentation', the term 'culture' includes 'a fermented product', and includes a culture solution itself (i.e., a culture solution itself containing bacteria) cultured in a medium or processed products derived from the culture solution itself, such as processed products obtained by heat treatment to the culture solution. Preferably, the culture of the present invention may be a culture solution containing the *Bifidobacterium breve* IDCC 4401 strain or a processed product obtained by heat treatment to the culture solution.

In the present invention, the composition may be included in any form including the *Bifidobacterium breve* IDCC 4401 (accession number: KCTC13169BP), culture thereof or a *Bifidobacterium breve* IDCC 4401 dead cell, and preferably, the composition may be a food composition or a pharmaceutical composition, but is not limited thereto.

When the composition is the food composition, the *Bifidobacterium breve* IDCC 4401 (accession number: KCTC13169BP), culture thereof or the *Bifidobacterium breve* IDCC 4401 dead cell may be added as it is or used together with other foods or food ingredients, and may be used appropriately according to conventional methods.

The food composition of the present invention includes all foods in the conventional sense, and includes all forms such as functional food, nutritional supplements, health food, and food additives. The type of food composition may be prepared in various forms according to general methods known in the art.

The food composition of the present invention may include a health functional food. The term "health functional food" used in the present invention refers to food prepared and processed in the form of tablets, capsules, powders, granules, liquids and pills by using raw materials or ingredients having functionalities useful to the human body. Here, the 'functionality' refers to regulating nutrients to the structure and function of the human body or to obtaining effects useful for health applications such as physiological action. The health functional food of the present invention may be prepared by methods which are commonly used in the art and may be prepared by adding raw materials and ingredients which are commonly added in the art in preparation.

In addition, formulations of the health functional food may also be prepared without limitations as long as the formulation is recognized as a health functional food. The food composition of the present invention may be prepared in various types of formulations, and unlike general drugs, the food composition has an advantage that there is no side effect that may occur when taking a long-term use of the drug by using the food as a raw material, and has excellent portability, but the health functional food of the present invention can be taken as supplements to enhance the effects of improving or treating dyslipidemia.

For example, the health functional food may be drunk in the form of tea, juice, and drinks including the *Bifidobacterium breve* IDCC 4401 of the present invention or dead cell thereof or taken by granulation, encapsulation and powdering. In addition, the *Bifidobacterium breve* IDCC 4401 of the present invention or dead cell thereof is combined with known substances or active ingredients known to have an effect of preventing, improving or treating dyslipidemia to be prepared in the form of the composition.

In addition, the food composition of the present invention may contain various nutrients, vitamins, electrolytes, flavoring agents, coloring agents, pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, or the like. In addition, the food composition of the present invention may contain pulp for preparing natural fruit juice, fruit juice beverage or vegetable beverage. These ingredients may be used independently or in combination. Although the ratio of these additives is not very important, generally, the ratio thereof is selected in a range of 0.01 to 0.3 part by weight per 100 parts by weight of the food composition of the present invention, but is not limited thereto.

In addition, the food composition of the present invention may contain various flavoring agents or natural carbohydrates as additional ingredients, like general beverage. The carbohydrates include monosaccharides such as glucose and fructose, disaccharides such as maltose and sucrose, polysaccharides such as dextrin and cyclodextrin, and sugar alcohols such as xylitol, sorbitol, and erythritol. As the sweetening agent, natural sweetening agents such as thaumatin and stevia extracts, synthetic sweetening agents such as saccharin and aspartame, and the like may be used. A ratio of the natural carbohydrates may be generally about 0.01 to 0.04 g, preferably about 0.02 to 0.03 g per 100 mL of the composition of the present invention, but is not limited thereto.

In the food composition of the present invention, a mixing amount of the *Bifidobacterium breve* IDCC 4401 live cells or dead cells thereof may be appropriately determined depending on the purpose of use (prevention, health, or therapeutic treatment). For example, when producing foods or beverages, the *Bifidobacterium breve* IDCC 4401 live cells of the present invention or dead cells thereof may be added in an amount of $1 \times 10^5$ to $1 \times 10^{11}$ (cell number), preferably $1 \times 10^6$ to $1 \times 10^{10}$ of the bacteria of the present invention per 1 g (or ml) of the specific food material, but are not limited thereto. In addition, a daily intake of the food composition containing the *Bifidobacterium breve* IDCC 4401 live cells or dead cells thereof is $1 \times 10^5$ to $1 \times 10^{10}$ CFU/kg, preferably $1 \times 10^6$ to $1 \times 10^9$ CFU/kg based on the number of cells, and the intake may be taken once a day or divided several times, but is not limited thereto.

In the food composition of the present invention, the effective amount of the strain may be used based on an effective amount of the pharmaceutical composition, but may be the range or less in the case of long-term intake for health and hygiene purposes or for health control, and it is certain that the active ingredient may be used even in an amount above the range because there is no problem in terms of safety.

In the present invention, when the composition is the pharmaceutical composition, the *Bifidobacterium breve* IDCC 4401 (accession number: KCTC13169BP), culture thereof or the *Bifidobacterium breve* IDCC 4401 dead cell may be contained alone or one or more pharmaceutically acceptable carriers, excipients or diluents may be further contained.

The pharmaceutically acceptable carrier may further include, for example, a carrier for oral administration or a carrier for parenteral administration. The carrier for oral administration may include lactose, starch, cellulose derivatives, magnesium stearate, stearic acid, and the like. In addition, the carrier for parenteral administration may include water, suitable oil, saline, aqueous glucose, glycol, and the like, and further include a stabilizer and a preservative. A suitable stabilizer includes antioxidants such as sodium hydrogen sulfite, sodium sulfite or ascorbic acid. A suitable preservative includes benzalkonium chloride, methyl- or propyl-paraben and chlorobutanol. Other pharmaceutically acceptable carriers may refer to those known in the art.

The pharmaceutical composition of the present invention may be administered to mammals including humans even by any method. For example, the pharmaceutical composition may be administered orally or parenterally. The parenteral administration method is not limited thereto, but may include intravenous, intramuscular, intraarterial, intramedullary, intrathecal, intracardiac, transdermal, subcutaneous, intraperitoneal, intranasal, enteral, topical, sublingual or rectal administration.

The pharmaceutical composition of the present invention may be formulated as formulations for oral administration or parenteral administration according to the route of administration as described above. In the case of the formulations for oral administration, the composition of the present invention may be formulated as powders, granules, tablets, pills, sugar-coated tablets, capsules, liquids, gels, syrups, slurry, suspensions, etc. by using methods known in the art. For example, the oral formulations may obtain tablets or sugar-coated tablets by mixing an active ingredient with a solid excipient, pulverizing the mixture, adding a suitable adjuvant, and then processing the mixture into a granular mixture. Examples of the suitable excipient may include sugars including lactose, dextrose, sucrose, sorbitol, mannitol, xylitol, erythritol and maltitol, starches including corn starch, wheat starch, rice starch and potato starch, celluloses including cellulose, methyl cellulose, sodium carboxymethylcellulose and hydroxypropylmethyl-cellulose, fillers such as gelatin, polyvinylpyrrolidone, and the like. In addition, in some cases, cross-linked polyvinylpyrrolidone, agar, alginic acid, sodium alginate, or the like may be added as a disintegrant. In addition, the pharmaceutical composition of the present invention may further include anti-coagulating agents, lubricants, wetting agents, flavorings, emulsifiers and antiseptics.

Formulations for parenteral administration may be formulated in the form of injections, creams, lotions, external ointments, oils, moisturizers, gels, aerosols and nasal inhalants by methods known in the art. These formulations are described in formulary commonly known in all pharmaceutical chemistry.

The total effective amount of the *Bifidobacterium breve* IDCC 4401 of the present invention or dead cell thereof may be administered to a patient in a single dose, or may be administered to the patient according to a fractionated treatment protocol administered in a multiple dose for a long period of time. In the pharmaceutical composition of the present invention, the content of the active ingredient may vary depending on the severity of disease. Preferably, a preferred total dose of the *Bifidobacterium breve* IDCC 4401 or dead cell thereof is about 0.01 μg to 1,000 mg, most preferably 0.1 μg to 100 mg per 1 kg of patient body weight per day based on a solid content. However, the dose of the *Bifidobacterium breve* IDCC 4401 of the present invention or dead cell thereof is determined as an effective amount to the patient by considering various factors including the age, body weight, health conditions, and sex of a patient, the severity of disease, diet, and release rate, in addition to an administration route and the number of treatment times of the pharmaceutical composition. Accordingly, considering such an aspect, those skilled in the art may determine a suitable effective amount of the strain of the present invention and dead cell thereof according to a specific use as a preventive, improving or therapeutic agent for dyslipidemia. The pharmaceutical composition according to the present invention is not particularly limited to the formulation, the administration route, and the administration method, as long as the effects of the present invention are shown.

In addition, the present invention provides a composition for controlling intestinal functions, a probiotic composition, a feed composition, and a fermented product comprising the strain or culture thereof as an active ingredient. When the composition is provided for controlling intestinal functions or feed, the strain of the present invention may be provided in the form of dead cells as well as live cells.

The *Bifidobacterium breve* IDCC 4401 strain of the present invention may be used for improving the health of humans and animals, that is, as a composition for controlling intestinal functions, probiotics, or feed. The composition includes the strain itself or culture thereof as an active ingredient, and may further include an excipient or a carrier. The content of the *Bifidobacterium breve* IDCC 4401 strain in the composition may vary depending on the use and formulation of the composition. The composition for controlling intestinal functions or the probiotic composition according to the present invention may be prepared and administered in various formulations and methods. For example, the *Bifidobacterium breve* IDCC 4401 strain or culture thereof is mixed with carriers and flavors commonly used in the pharmaceutical field to be prepared and administered in the form of tablets, troches, capsules, elixir, syrups, powders, suspensions, granules, or the like. As the carrier, binders, lubricants, disintegrants, excipients, solubilizers, dispersants, stabilizers, suspending agents, and the like may be used.

The administration method may use oral, parenteral or application methods, preferably oral administration. In addition, the dose may be appropriately selected depending on the degree of absorption, inactivity rate and release rate of an active ingredient in the body, age, sex, and conditions of a recipient, and the like.

In addition, the feed composition according to the present invention may be prepared in the form of fermented feed, formulated feed, pellet form and silage. The fermented feed may be prepared by adding the *Bifidobacterium breve* IDCC 4401 strain of the present invention and various microorganisms or enzymes to ferment an organic material, and the formulated feed may be prepared by mixing various types of general feed and the *Bifidobacterium breve* IDCC 4401 strain of the present invention. The pellet-type feed may be prepared by formulating the fermented feed or formulated feed with a pellet machine, and the silage may be prepared by fermenting green feed with the *Bifidobacterium breve* IDCC 4401 strain according to the present invention.

The *Bifidobacterium breve* IDCC 4401 strain according to the present invention or culture thereof may be used as a food additive for foods such as kimchi, beverages, and baby food. In addition, the *Bifidobacterium breve* IDCC 4401 strain of the present invention may be used as a starter for producing a fermented product. The 'fermented product' may be used interchangeably with the term 'fermented food' in this specification. The fermented product is food that requires a fermentation process during production, and the type thereof is not limited as long as the fermented product is known in the art. For example, the fermented product includes cheese, yogurt, butter, cream, ice cream, lactic beverages, kefir, fermented milk, kimchi, fermented raw food products, etc. A fermented product using the *Bifidobacterium breve* IDCC 4401 strain of the present invention may be prepared according to a conventional method known in the art. The producing method of the fermented product usually consists of processes, such as preparation of raw materials, addition of lactic acid bacteria, fermentation, recovery of a finished product, and the like. The step of preparing the raw materials is a step of preparing materials to be fermented and preparing fermentation conditions so that fermentation may be performed well. The addition of the lactic acid bacteria is the addition of an appropriate amount of bacteria according to an amount to be fermented, and the present invention is characterized in that *Bifidobacterium breve* IDCC 4401 strain is used. The fermentation may be performed according to conventional fermentation conditions of fermenting bacteria, and may be performed, for example, at 20° C. to 40° C. for 1 to 168 hours. The recovery of the finished product includes all post-processing processes and packaging to facilitate storage and transportation, from removing unnecessary by-products or unfermented materials from fermented products.

As a specific example, the *Bifidobacterium breve* IDCC 4401 strain according to the present invention may be used to prepare lactic beverages. The lactic beverage may be a product obtained by culturing the *Bifidobacterium breve* IDCC 4401 strain of the present invention, fermenting the strain with lactic acid, diluting with sterilized water, adding sugar, a flavoring, and the like, and then filling the mixture into a container. Since these beverages generally contain live lactic acid bacteria, the beverages can be expected to have an intestinal controlling function in the intestines after drinking.

In addition, fermented raw food products may be prepared by treating grain powder such as brown rice and adlay with the *Bifidobacterium breve* IDCC 4401 strain according to the present invention or 2 to 3 kinds of mixed lactic acid bacteria including the strain, fermenting at an appropriate temperature, and then appropriately mixing various agricultural products such as white rice, glutinous rice, and sorghum to ensure excellent nutritional balance and palatability.

The present invention provides a use of a *Bifidobacterium breve* IDCC 4401 strain (accession number: KCTC13169BP), culture thereof or a *Bifidobacterium breve* IDCC 4401 dead cell for preparing an agent for treating dyslipidemia.

The present invention provides a method for treating dyslipidemia comprising administering an effective amount of an agent comprising at least one of a *Bifidobacterium breve* IDCC 4401 strain (accession number: KCTC13169BP), culture thereof or a *Bifidobacterium breve* IDCC 4401 dead cell to a subject in need thereof.

The term 'effective amount' of the present invention means an amount that exhibits effects of improving, treating, preventing, detecting, and diagnosing dyslipidemia, or inhibiting or alleviating dyslipidemia when administered to the subject. The 'subject' may be animals, preferably, mammals, particularly animals including humans, and may also be cells, tissues, organs, and the like derived from animals. The subject may be a patient requiring the effects.

The 'treatment' of the present invention comprehensively refers to improving dyslipidemia or symptoms of dyslipidemia, and may include treating or substantially preventing the disease, or improving the conditions thereof and includes palliating, treating or preventing a symptom or most of symptoms derived from the disease, but is not limited thereto.

The term "comprising" used herein is used in the same meaning as "including" or "characterized by", and does not exclude additional ingredients or steps of the method, which are not specifically mentioned in the composition or the method according to the present invention. In addition, the term "consisting of" means excluding additional elements, steps or ingredients, etc., unless otherwise described. The term "essentially consisting of" means including materials or steps which do not substantially affect basic properties thereof in addition to the described materials or steps within the range of the composition or the method.

The novel *Bifidobacterium breve* IDCC 4401 strain (accession number: KCTC13169BP) of the present invention not only has an excellent cholesterol-reducing effect in the body, but also has a very high level of acid tolerance and bile tolerance unlike previously known *B. breve* strains to exhibit well the functionality of the strain in the digestive duct of animals (especially humans), have an excellent growth potential, and provide sustainable and effective functionality of reducing cholesterol in vivo.

In addition, not only the strain but also the dead cell ID-BBR4401 prepared by heat treatment thereto have excellent cholesterol-binding ability equivalent to that of live cells, and have a high level of binding ability with bile acids to show a remarkable effect of release of bile acids in vitro. Accordingly, the strain or dead cell thereof ID-BBR4401 of the present invention not only has a very excellent reducing effect of cholesterol in vivo, particularly LDL-cholesterol, but also has a remarkable reducing effect of triglycerides in vivo (especially, in the liver), thereby exhibiting an excellent effect of preventing and treating dyslipidemia.

Hereinafter, the present invention will be described in detail.

However, the following Examples are just illustrative of the present invention, and the contents of the present invention are not limited to the following Examples.

Example 1: Isolation and Identification of Novel Strain

In order to develop lactic acid strains, the present inventors sequentially diluted infant feces with saline using a decimal dilution method, smeared the diluted feces on an MRS medium (BD, 288210), cultured anaerobically the strains at 37° C. for 2 days, observed the strains, and isolated and confirmed strains for formed colonies.

Among a plurality of isolated strains, an IDCC 4401 strain was finally selected and identified and analyzed. A carbohydrate fermentation pattern of the selected strain was determined using an API 50 CH identification kit (bioMerieux Vitex, Inc, France), and the strain was identified based on a 16S rRNA gene sequence.

The carbohydrate fermentation pattern of the IDCC 4401 strain was shown in Table 1 below, and as a result of 16S rRNA analysis, it was confirmed that the IDCC 4401 strain consisted of a sequence of SEQ ID NO: 1, and had 99% homology with *Bifidobacterium breve* to be identified as the same species. The identified novel microorganism of the present invention was deposited as '*Bifidobacterium breve* IDCC 4401' (KCTC 13169BP) on Dec. 2, 2016 at the Korean Collection for Type Cultures of the Korea Research Institute of Bioscience and Biotechnology, located at 52, Eoeun-dong, Yuseong-gu, Daejeon, Korea.

TABLE 1

| Acidification of carbohydrates | |
| --- | --- |
| Carbohydrates | Acidification |
| L-Arabinose | − |
| D-Xylose | − |
| Mannose | + |
| Mannitol | + |
| Sorbitol | + |
| a-Metylglucoside | − |
| Amygdalin | + |
| Arbutin | w |
| Esculin hydrolysis | + |
| Salicin | − |

TABLE 1-continued

| Acidification of carbohydrates | |
| --- | --- |
| Carbohydrates | Acidification |
| Trehalose | – |
| Melezitose | – |
| Starch | + |
| Glycogen | + |

(+, Positive; –, negative; w, weak positive)

Example 2: Selection of Strains with Excellent Cholesterol-Lowering Effect

In order to select strains with an excellent cholesterol-lowering effect, the cholesterol binding ability was first confirmed for 20 types of probiotics owned by Ildong Pharmaceutical, including the strain identified in Example 1 above. Among the strains, a second test was conducted only for 8 types of probiotics confirmed to have the cholesterol binding ability (see Table 2 and FIG. 1 below).

The cholesterol-lowering effect of strain agents shown in Table 2 below was measured by the following method. First, 1% (v/v) of each strain (experimental group) was inoculated into 10 ml of an MRS medium (BD, MRS broth) containing 10% cholesterol. After 48 hr of inoculation, only a supernatant was collected by centrifugation, and each residual cholesterol concentration was measured.

Figure 1:
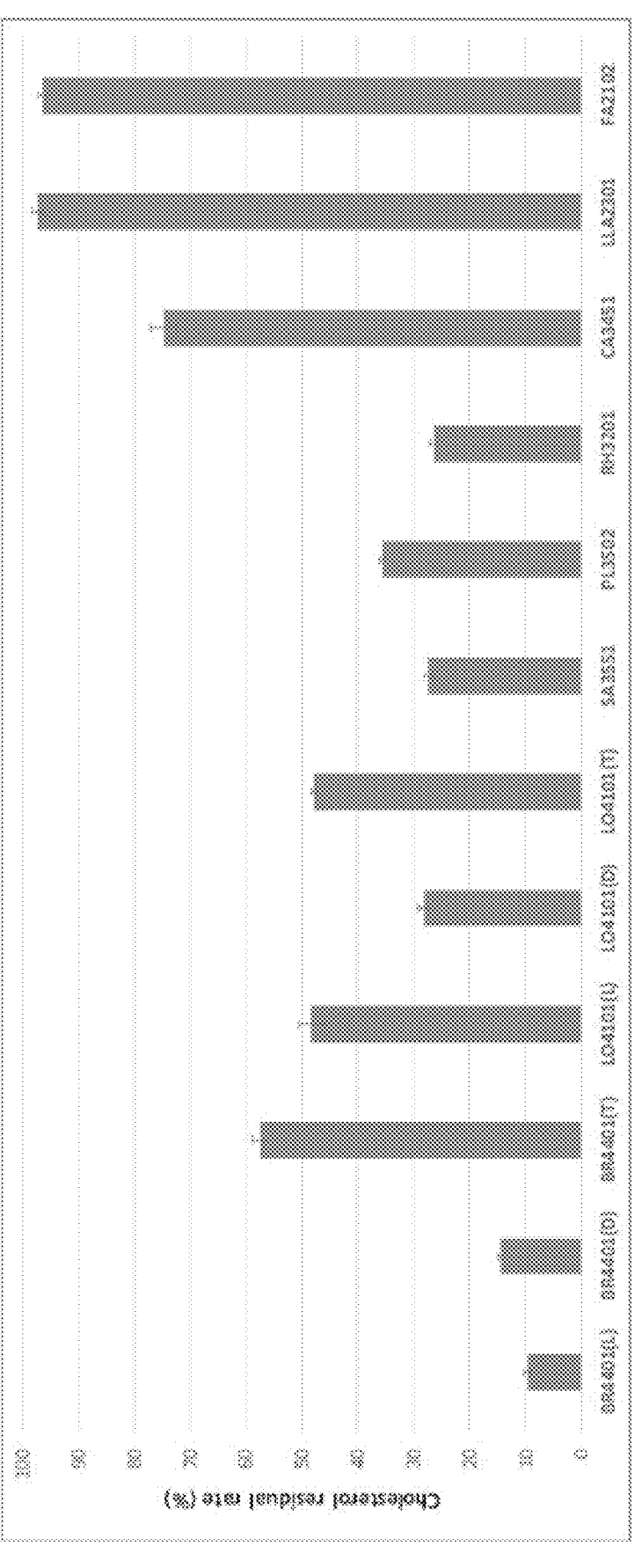
FIG. 1 illustrates results of comparative evaluation of the cholesterol-specific binding ability of live cells with respect to various bacterial species, including a novel strain of the present invention.

As experimental results, as shown in FIG. 1, a *Bifidobacterium breve* IDCC 4401 live cell experimental group identified in Example 1 had the lowest residual cholesterol. Table 2 showed the results of measuring a cholesterol residual rate for each strain.

TABLE 2

| Strain-specific choresterol residual rate | | | |
| --- | --- | --- | --- |
| Experimental group | Strain name | Formulation | Choresterol residual rate % (w/w) |
| Control | — | — | 100 |
| BR4401 (L) | *Bifidobacterium breve* IDCC4401 | Live cell | 9.6 ± 0.5 |
| LO4101 (L) | *Bifidobacterium longum* IDCC4101 | Live cell | 48.3 ± 2.4 |
| SA3551 | *Lactobacillus salivarius* IDCC3551 | Live cell | 27.4 ± 0.7 |
| PL3502 | *Lactobacillus plantarum* IDCC3502 | Live cell | 35.6 ± 0.5 |
| RH3201 | *Lactobacillus rhamnosus* IDCC3201 | Live cell | 26.3 ± 0.9 |
| CA3451 | *Lactobacillus casei* IDCC3451 | Live cell | 74.8 ± 2.2 |
| LLA2301 | *Lactococcus lactis* IDCC2301 | Live cell | 97.3 ± 1.0 |
| FA2102 | *Enterococcus faecium* IDCC2101 | Live cell | 96.4 ± 0.8 |

Example 3: Process of Preparing Dead Cell

In order to prepare an optimal *Bifidobacterium breve* IDCC4401 dead cell ID-BBR4401 with excellent cholesterol binding ability, an experiment was conducted on heating (70 to 110° C.) conditions. The centrifuged cells were added with distilled water of 1 to 2 times the weight of the centrifuged cells, suspended, heated for 1 hour at each temperature condition as shown in Table 3 below, and then freeze-dried to prepare dead cells for each condition. From this, the optimal conditions for dead cells were selected through the number of cells measured through a hemocytometer and a general bacterial test, and the measurement results were shown in Table 3 below.

TABLE 3

| Cell number for each heating condition and general bacteria test results | | | |
| --- | --- | --- | --- |
| Condition | Temperature (° C.) | Cell number (×$10^{11}$ cells/g) | General bacteria |
| 1 | 70 | 5.712 | + |
| 2 | 80 | 5.696 | – |
| 3 | 90 | 5.680 | – |
| 4 | 100 | 4.967 | – |
| 5 | 110 | 4.688 | – |

As a result of the experiment, as shown in Table 3, it was confirmed that the heating condition at 80 to 90° C. was most suitable as a condition for maintaining a high level of homogeneous properties of *B. breve* IDCC4401 of the present invention while removing general bacteria. The dead cell produced by heating at 80 to 90° C. was referred to as ID-BBR4401 in the present specification.

The selected *Bifidobacterium breve* IDCC 4401 dead cell was referred to as 'ID-BBR4401' (see FIG. 2), and a scanning electron microscope image thereof was shown in FIG. 3. In addition, FIG. 4 shows results obtained by photographing the binding of ID-BBR4401 to cholesterol through a scanning electron microscope.

Example 4: Comparison of Cholesterol-Reducing (Lowering) Ability Between the Same Strain Species In order to confirm an excellent cholesterol-lowering effect of a *Bifidobacterium breve* IDCC 4401 live cell of the present invention and a dead cell ID-BBR4401, a comparison experiment was conducted on cholesterol binding ability with different strains of the same strain species known to have a cholesterol-lowering effect in the related art. Specifically, as shown in Table 4 and FIG. 5 below, a total of 5 strains was experimented, added and suspended with distilled water 1 to 2 times of the cell weight of the strains, and then heated at 80 to 90° C. for 1 hour and freeze-dried to be killed, and thereafter, the effects of live and dead cells were evaluated. The cholesterol-lowering effect was confirmed in the same manner as in Example 2 above. 1% (v/v) of live and dead cells of each strain were inoculated into 10 ml of an MRS medium containing cholesterol. After 48 hr of inoculation, only a supernatant was collected by centrifugation, and each residual cholesterol concentration was measured.

TABLE 4

| Comparison of cholesterol residual rate between same strain species | | |
| --- | --- | --- |
| | Residual rate (%) | |
| Strain name | Live cell | Dead cell |
| *Bifidobacterium breve* IDCC 4401 | 9.2 ± 0.1 | 14.3 ± 1.0 |
| *Bifidobacterium breve* Morinaga B-3 | 71.8 ± 1.3 | 75.0 ± 2.6 |
| *Bifidobacterium breve* ATCC15700 | 31.1 ± 0.8 | 36.2 ± 1.4 |
| *Bifidobacterium breve* ATCC15698 | 87 ± 2.1 | 91.4 ± 2.8 |
| *Bifidobacterium breve* NCIMB8807 | 23.8 ± 0.6 | 33.0 ± 1.5 |

As a result of the experiment, the results of measuring the cholesterol residual rate for each strain were shown in Table 4 above. It was considered that the case of dead cells, the number of cells maintained the level at the time of initial introduction, but in the case of live cells, the cells grew during the culture period and the number of cells was relatively higher than that of the dead cells, and thus, numerically, the cholesterol residual may be slightly lower. At this time, it was confirmed that a *Bifidobacterium breve* IDCC 4401 dead cell ID-BBR4401 of the present invention had the lowest residual cholesterol per same cell unit number, which was significantly different from other strains at a significant level.

Moreover, in the case of a *B. breve* NCIMB8807 strain, it was found that the cholesterol binding ability of dead cells was significantly lowered compared to the live cells. On the other hand, the *B. breve* IDCC 4401 dead cell ID-BBR4401 of the present invention showed better cholesterol binding ability at the same level as its live cell or at a higher level there than, and particularly, the ID-BBR4401 of the present invention had very significantly excellent cholesterol-lowering ability compared to live cells of other *B. breve* strains. Therefore, it was confirmed that the agents of *Bifidobacterium breve* IDCC 4401 live cell and dead cell ID-BBR4401 had the best cholesterol binding ability, and was also considered to have excellent stability.

Example 5: Comparison of Bile Acid-Reducing (Lowering) Ability Between the Same Strain Species In order to confirm an excellent bile acid-lowering effect of a *Bifidobacterium breve* IDCC 4401 live cell of the present invention and a dead cell ID-BBR4401, a comparison experiment was conducted with different strains of the same strain species. A total of 5 strains were all killed, and then effects of live cells and the dead cells of each strain were evaluated. 10% (v/v) of each strain was inoculated into 10 ml of an MRS medium containing bile acid. After 24 hr of inoculation, only a supernatant was collected by centrifugation, and each residual bile acid concentration was measured. As a result of the experiment, the results of measuring the residual bile acid ratio for each strain were shown in Table 5 and FIG. 6 below. It was confirmed that *Bifidobacterium breve* IDCC 4401 of the present invention had the lowest residual bile acid in both live and dead cells, which had a significant difference from other strains.

TABLE 5

| Comparison of bile acid residual rate between same strain species | | |
|---|---|---|
| | Residual rate (%) | |
| Strain name | Live cell | Dead cell |
| *Bifidobacterium breve* IDCC 4401 | 32.57 ± 1.4 | 57.6 ± 2.8 |
| *Bifidobacterium breve* Morinaga B-3 | 80.4 ± 1.5 | 79.2 ± 2.8 |

TABLE 5-continued

| Comparison of bile acid residual rate between same strain species | | |
|---|---|---|
| | Residual rate (%) | |
| Strain name | Live cell | Dead cell |
| *Bifidobacterium breve* ATCC15700 | 33.7 ± 1.6 | 62.9 ± 3.8 |
| *Bifidobacterium breve* ATCC15698 | 89.9 ± 5.0 | 96.3 ± 1.5 |
| *Bifidobacterium breve* NCIMB8807 | 54.9 ± 0.4 | 68.6 ± 6.5 |

Example 6: Confirmation of Acid Tolerance and Bile Tolerance Characteristics In order to confirm that the *Bifidobacterium breve* IDCC 4401 of the present invention was not affected by acid and bile acid, acid tolerance and bile tolerance experiments were conducted. If an effect of gastric acid and bile acid to live cells is small, the effect of gastric acid and bile acid will be small even in the dead cell state. Accordingly, in the experiment, the *Bifidobacterium breve* IDCC 4401 live cells were used, and compared and evaluated with different strains of the same species, as shown in Tables 6 and 7 below.

In the acid tolerance experiment, 1% (v/v) of the strain was inoculated into 10 ml of an MRS medium adjusted to pH 2.5, pH 3.0 and pH 7.0 with hydrochloric acid, respectively. After 24 hours of inoculation, the number of cells in each culture medium was checked and the difference thereof was compared. The measured result thereof was shown in Table 5 below.

For bile tolerance, 1% (v/v) of the strain was inoculated into 10 ml of an MRS medium containing 0.1 to 0.5% (w/v) of Oxgall, respectively. After 24 hours of inoculation, the number of cells in each culture medium was checked and the difference thereof was compared. The measured results thereof were shown in Tables 6 and 7 below.

TABLE 6

| Bile tolerance comparison test between *Bifidobacterium breve* strains (×10⁹ cfu/ml) | | | |
|---|---|---|---|
| | pH | | |
| Strain name | 2.5 | 3.0 | 7.0 |
| *Bifidobacterium breve* IDCC4401 | 5.9 ± 0.7 | 5.9 ± 0.4 | 6.0 ± 0.2 |
| *Bifidobacterium breve* ATCC15700* | 4.8 ± 1.2 | 5.1 ± 0.7 | 6.2 ± 0.8 |
| *Bifidobacterium breve* Morinaga B-3 | 2.7 ± 0.5 | 3.5 ± 1.1 | 6.1 ± 1.5 |
| *Bifidobacterium breve* ATCC15698 | 2.9 ± 1.3 | 3.7 ± 0.3 | 5.9 ± 0.7 |
| *Bifidobacterium breve* NCIMB8807 | 3.0 ± 0.6 | 4.0 ± 0.5 | 5.9 ± 1.2 |

TABLE 7

| Bile tolerance comparison test between *Bifidobacterium breve* strains (×10⁹ cfu/ml) | | | | | |
|---|---|---|---|---|---|
| | Oxgall concentration(%) | | | | |
| Strain name | 0.1 | 0.2 | 0.3 | 0.4 | 0.5 |
| *Bifidobacterium breve* IDCC4401 | 6.1 ± 0.5 | 6.0 ± 0.2 | 5.8 ± 0.4 | 5.9 ± 0.3 | 5.9 ± 0.6 |
| *Bifidobacterium breve* ATCC15700* | 6.0 ± 0.3 | 5.0 ± 0.7 | 3.2 ± 0.6 | 2.1 ± 0.7 | 2.0 ± 0.2 |
| *Bifidobacterium breve* Morinaga B-3 | 5.8 ± 0.5 | 4.8 ± 0.2 | 2.9 ± 0.3 | 1.8 ± 0.3 | 1.7 ± 0.2 |

TABLE 7-continued

| Bile tolerance comparison test between *Bifidobacterium breve* strains ($\times 10^9$ cfu/ml) | | | | | |
|---|---|---|---|---|---|
| | Oxgall concentration(%) | | | | |
| Strain name | 0.1 | 0.2 | 0.3 | 0.4 | 0.5 |
| *Bifidobacterium breve* ATCC15698 | 6.2 ± 0.7 | 4.9 ± 0.7 | 3.5 ± 0.3 | 2.2 ± 0.4 | 1.9 ± 0.2 |
| *Bifidobacterium breve* NCIMB8807 | 5.9 ± 0.2 | 5.1 ± 0.6 | 3.3 ± 0.5 | 2.7 ± 0.2 | 2.0 ± 0.1 |

As shown in Tables 6 and 7, it was confirmed that the *B. breve* IDCC4401 strain of the present invention showed a high level of acid tolerance and bile tolerance compared to other strains.

Example 7: Thermal Stability Confirmation Test

When a ID-BBR4401 composition, which was a dead cell of *Bifidobacterium breve* IDCC4401 with excellent cholesterol binding ability, was stored for a long time in various temperature environments, an experiment was conducted to determine whether there was a change in the number of cells containing in the composition and a change in the cholesterol-binding activity. The number of cells was measured using a hemocytometer, and the number of cells measured for each period was compared. The activity was compared through the residual rate by conducting a cholesterol-lowering effect test in the same manner as in Example 2. The result thereof was shown in Table 8 below.

TABLE 8

| Thermal stability of ID-BBR4401 at high-temperature environment (45° C.) | | | | | |
|---|---|---|---|---|---|
| | 4° C. | | 25° C. | | 45° C. | |
| Period (month) | Cell number ($\times 10^{10}$ cells/g) | Residual rate (%) | Cell number ($\times 10^{10}$ cells/g) | Residual rate (%) | Cell number ($\times 10^{10}$ cells/g) | Residual rate (%) |
| 0 | 1.15 ± 0.07 | 14.3 ± 0.5 | 1.15 ± 0.07 | 14.3 ± 0.5 | 1.15 ± 0.07 | 14.3 ± 0.5 |
| 3 | 1.11 ± 0.03 | 14.9 ± 0.6 | 1.09 ± 0.04 | 14.0 ± 0.1 | 1.10 ± 0.04 | 14.6 ± 0.7 |
| 6 | 1.09 ± 0.09 | 14.8 ± 0.7 | 1.12 ± 0.09 | 14.1 ± 0.3 | 1.11 ± 0.09 | 14.7 ± 1.2 |
| 9 | 1.07 ± 0.04 | 14.4 ± 0.4 | 1.10 ± 0.11 | 14.9 ± 1.1 | 1.13 ± 0.11 | 14.2 ± 0.7 |
| 12 | 1.11 ± 0.05 | 14.9 ± 0.8 | 1.05 ± 0.03 | 14.7 ± 0.9 | 1.09 ± 0.05 | 14.5 ± 0.9 |
| 18 | 1.12 ± 0.03 | 14.3 ± 0.2 | 1.08 ± 0.02 | 14.9 ± 1.2 | 1.14 ± 0.10 | 14.6 ± 0.2 |
| 24 | 1.01 ± 0.02 | 14.8 ± 0.7 | 1.14 ± 0.11 | 14.5 ± 0.3 | 1.10 ± 0.07 | 14.2 ± 0.2 |

As the experimental result, as shown in Table 6, it was confirmed that the ID-BBR4401 of the present invention had excellent long-term stability and thermal stability.

Example 8: Evaluation of Efficacy in Dyslipidemia Animal Model 8-1. Establishment of Dyslipidemia (Hyperlipidemia) Animal Model Five-week-old male SD rats (Orient Bio Inc.) were purchased and used after a one-week acclimatization period. The experiment was conducted in an animal room in which constant temperature (22±2° C.) and constant humidity (50 to 60%) were maintained, and a photoperiod (08:00 to 20:00) and a dark period (20:00 to 08:00) were maintained at 12-hour intervals. Test animals were accommodated in a breeding cage by 3 rats per group, and sterilized feed and primary distilled water were freely supplied. A total of 54 rats were used in the experiment in 6 groups of 9 rats per test substance, and each group was normal (ND), vehicle (only high-fat diet. HCD), positive control (Rosuvastatin 10 mg/kg/2 mL administration, HCD+R), ID-BBR4401 $1\times10^6$ cells/rat administered group (HCD+L), ID-BBR4401 $1\times10^7$ cells/rat administered group (HCD+M), and ID-BBR4401 $1\times10^8$ cells/rat administered group (HCD+H). As a feed for inducing hypercholesterolemia, a high cholesterol diet (HCD) feed in which 43% of the total calories in the diet was composed of fat, and 1.25% of cholesterol and 0.5% of cholic acid were added was provided during the test period. The diet was provided twice a week so that there was no shortage of diet.

8-2. Dyslipidemia (Hyperlipidemia) Animal Model Test

During a supply period of HCD, Rosuvastatin 10 mg/kg/dau was administered to the positive control group, and ID-BBR4401 was prepared at $1\times10^6$ cells/rat/day, $1\times10^7$ cells/rat/day, and $1\times10^8$ cells/rat/day, respectively, and administered orally 5 times (Monday to Friday) a week for 6 weeks. After 6 weeks of drug administration was completed, the animals were fasted for 12 hours before necropsy, and then anesthetized by inhalation with ether, and blood was obtained from the abdominal vena cava. Thereafter, the blood was added in a 15 ml comical tube and centrifuged at 3,000 rpm and 4° C. for 10 minutes to obtain serum. In addition, the liver was isolated, weighed, and partially separated and frozen in liquid nitrogen and stored at −70° C.

8-3. Measurement of Blood Lipid Indicators

Blood lipid indicators were triglyceride (TG), total cholesterol (TC), high density lipoprotein cholesterol (HDL-C), and low density lipoprotein cholesterol (LDL-C). Blood lipid levels were measured using the serum obtained at autopsy. The blood indicators were measured according to a kit protocol using the TG, TC, and HDL-C kits (Asan Pharmaceutical), and in the case of LDL-C, the result values of TG, TC, and HDL-C measured using the kits were calculated using the Fridewald formula (LDL-C=TC−HDL-C−(TG/5)).

As a result of measuring the blood lipids, as shown in FIG. 7, it was confirmed that the ID-BBR4401 $1\times10^7$ cells/rat/day (HCD+M) and $1\times10^8$ cells/rat/day (HCD+H) administered groups showed a significant reduction in blood TC and LDL-C as compared to the vehicle administered group to have an excellent effect of improving hyperlipidemia and hypercholesterolemia.

8-4. Measurement of Hepatic Lipid Indicators

Hepatic lipid indicators were hepatic triglyceride (hepatic-TG) and hepatic total cholesterol (hepatic-TC). The liver tissue obtained at autopsy was added with a chloroform:methanol (2:1) solution in a 10 times volume of the weight of the liver tissue, crushed using a homogenizer, and then added with the same amount of physiological saline (0.9% NaCl) as methanol, vortexed for 1 minute, and then centrifuged (2000 rpm, 20 min) to obtain a chloroform layer. The obtained chloroform layer was added with the same amount of chloroform:methanol:3 mM sodium cholate (3:24:25), vortexed for 1 minute, and then centrifuged to separate a chloroform layer. The obtained chloroform layer was evaporated in a water bath at 80° C. for 30 minutes to obtain a lipid extract. TG and TC of the obtained lipid were measured according to a kit protocol using TG and TC kits of Asan Pharmaceutical.

As a result of measuring the hepatic lipids, as shown in FIG. 8, liver hepatic-TC was significantly reduced in ID-BBR4401 $1 \times 10^7$ cells/rat/day (HCD+M) and $1 \times 10^8$ cells/rat/day (HCD+H) administered groups among the ID-BBR4401 administered groups to confirm the effect of improving hypercholesterolemia. In addition, in the ID-BBR4401 administered group of the present invention, the amount of hepatic-TG (triglyceride) was decreased in a dose-dependent manner, and in particular, the $1 \times 10^8$ cells/rat/day administered group exhibited the best hepatic-TG reduction effect.

8-5. Measurement of Fecal Bile Acid Indicators

Before three days at the end of the test, feces were received from each individual, weighed, and frozen. From the frozen feces, moisture were removed by freeze-drying. A lipid extract was obtained from the dried feces in the same manner as in Example 7-4. The obtained lipid was measured according to the kit protocol using a bile acid measurement kit (Rat Total Bile Acids Assay Kit, Crystal Chem).

As the experimental result, as shown in FIG. 9, the bile acid content from the feces in each experimental group increased compared to the vehicle in all ID-BBR4401 administered groups, the amount of bile acid had a high level compared to the Rosuvastatin administered group, and the amount of bile acid increased in a concentration-dependent manner, so that the most bile acid was released in the $1 \times 10^8$ cells/rat/day administered group (HCD+H). Accordingly, it was confirmed that ID-BBR4401 reduced the level of cholesterol in vivo by releasing the cholesterol out of the body by specifically binding to bile acids as a precursor. The fact is distinguished from a mechanism in which lactic acid bacteria probiotics known to have cholesterol-lowering ability in the related art deconjugated bile acids secreted into the small intestine through bile salt hydrolase (BSH) activity to be converted to free bile acids and these free bile acids were less reabsorbable than conjugated bile acids to be released out of the body. Since the ID-BBR4401 of the present invention, which is a dead cell agent, has no BSH activity, the above data show that the ID-BBR4401 agent of the present invention has very excellent bile acid binding ability.

Through Examples described above, the ID-BBR4401 dead cell agent of the present invention is characterized to have the ability of adsorbing cholesterol at a level of its live cell level or more and have the excellent binding ability to bile acids. Accordingly, it was confirmed that the ID-BBR4401 dead cell agent not only had very significant ability of reducing cholesterol (especially LDL-cholesterol) in the body, but also had the effect of reducing triglycerides in the body (especially liver), thereby exhibiting an excellent effect of preventing and treating dyslipidemia.

As described above, the present invention relates to a novel *Bifidobacterium breve* IDCC 4401 strain (accession number: KCTC13169BP) and dead cell thereof ID-BBR4401, which are excellent in acid tolerance and bile tolerance and have a preventive or therapeutic effect on dyslipidemia. The novel *Bifidobacterium breve* IDCC 4401 strain (accession number: KCTC13169BP) of the present invention not only has an excellent cholesterol-reducing effect in the body, but also has a very high level of acid tolerance and bile tolerance unlike previously known *B. breve* strains to exhibit well the functionality of the strain in the digestive duct of animals (especially humans), have an excellent growth potential, and provide sustainable and effective functionality of reducing cholesterol in vivo. In addition, the dead cell ID-BBR4401 prepared by heat treatment to the strain has excellent cholesterol-binding ability equivalent to that of live cells, and has a high level of binding ability with bile acids to show a remarkable effect of release of bile acids in vitro. Accordingly, the ID-BBR4401 of the present invention not only has a very excellent reducing effect of cholesterol in vivo, particularly LDL-cholesterol, but also has a remarkable reducing effect of triglycerides in vivo to exhibit an excellent effect of preventing and treating dyslipidemia, and thus has high industrial applicability in related fields such as medicine and health functional food.

Accession Number

Depositary Institute Name and Address: Korea Research Institute of Bioscience and Biotechnology, Korea Research Institute of Bioscience and Biotechnology (KRIBB), 181, Ipsin-gil, Jeongeup-si, Jeollabuk-do (56212)

Accession number: KCTC13169BP

Accession Date: 20161202

20

What is claimed is:

1. A method of treating dyslipidemia comprising administering to a mammalian subject in need thereof a composition comprising an effective amount of at least one of the isolated *Bifidobacterium breve* IDCC 4401 strain having the accession number KCTC13169BP, a culture thereof, or a heat-treated dead cell of the isolated *Bifidobacterium breve* IDCC 4401 strain.

* * * * *

SEQUENCE LISTING

```
Sequence total quantity: 1
SEQ ID NO: 1            moltype = RNA   length = 1402
FEATURE                Location/Qualifiers
source                 1..1402
                       mol_type = rRNA
                       organism = Bifidobacterium breve
rRNA                   1..1402
                       note = 16S rRNA sequence of Bifidobacterium breve IDCC 4401
SEQUENCE: 1
tgcagtcgaa cgggatccat cgggctttgc ctggtggtga gagtggcgaa cgggtgagta   60
atgcgtgacc gacctgcccc atgcaccgga atagctcctg gaaacgggtg gtaatgccgg  120
atgctccatc acaccgcatg gtgtgttggg aaagcctttg cggcatggga tggggtcgcg  180
tcctatcagc ttgatggcgg ggtaacggcc caccatggct tcgacgggta gccggcctga  240
```

-continued

```
gagggcgacc ggccacattg ggactgagat acggcccaga ctcctacggg aggcagcagt   300
ggggaatatt gcacaatggg cgcaagcctg atgcagcgac gccgcgtgag ggatggaggc   360
cttcgggttg taaacctctt ttgttaggga gcaaggcact ttgtgttgag tgtacctttc   420
gaataagcac cggctaacta cgtgccagca gccgcggtaa tacgtagggt gcaagcgtta   480
tccggaatta ttgggcgtaa agggctcgta ggcggttcgt cgcgtccggt gtgaaagtcc   540
atcgcttaac ggtggatccg cgccgggtac gggcgggctt gagtgcggta ggggagactg   600
gaattcccgg tgtaacggtg gaatgtgtag atatcgggaa gaacaccaat ggcgaaggca   660
ggtctctggg ccgttactga cgctgaggag cgaaagcgtg gggagcgaac aggattagat   720
accctggtag tccacgccgt aaacggtgga tgctggatgt ggggcccgtt ccacgggttc   780
cgtgtcggag ctaacgcgtt aagcatcccg cctggggagt acggccgcaa ggctaaaact   840
caaagaaatt gacgggggcc cgcacaagcg gcggagcatg cggattaatt cgatgcaacg   900
cgaagaacct tacctgggct tgacatgttc ccgacgatcc cagagatggg gtttcccttc   960
ggggcgggtt cacaggtggt gcatggtcgt cgtcagctcg tgtcgtgaga tgttgggtta   1020
agtcccgcaa cgagcgcaac cctcgccccg tgttgccagc ggattatgcc gggaactcac   1080
gggggaccgc cggggttaac tcggaggaag gtggggatga cgtcagatca tcatgcccct   1140
tacgtccagg gcttcacgca tgctacaatg gccggtacaa cgggatgcga cagcgcgagc   1200
tggagcggat ccctgaaaac cggtctcagt tcggatcgca gtctgcaact cgactgcgtg   1260
aaggcggagt cgctagtaat cgcgaatcag caacgtcgcg gtgaatgcgt tcccgggcct   1320
tgtacacacc gcccgtcaag tcatgaaagt gggcagcacc cgaagccggt ggcctaaccc   1380
cttgcgggag ggagccgtct aa                                            1402
```